(12) United States Patent
Kessel et al.

(10) Patent No.: US 7,744,945 B2
(45) Date of Patent: Jun. 29, 2010

(54) METHOD OF TABLET ENROBING

(75) Inventors: Stephen Ronald Kessel, Warboys (GB);
Ian David Povey, Stamford (GB);
Edward Zbygniew Nowak, Impington (GB)

(73) Assignee: BioProgress Technology International, Inc., Atlanta, GA (US)

( * ) Notice: Subject to any disclaimer, the term of this patent is extended or adjusted under 35 U.S.C. 154(b) by 789 days.

(21) Appl. No.: 10/477,570

(22) PCT Filed: May 29, 2002

(86) PCT No.: PCT/GB02/02506

§ 371 (c)(1),
(2), (4) Date: Nov. 10, 2003

(87) PCT Pub. No.: WO02/098394

PCT Pub. Date: Dec. 12, 2002

(65) Prior Publication Data
US 2004/0161527 A1    Aug. 19, 2004

(30) Foreign Application Priority Data
Jun. 2, 2001    (GB) .................................. 0113403.0

(51) Int. Cl.
*B05D 3/00* (2006.01)
(52) U.S. Cl. .................................... 427/2.14; 427/212
(58) Field of Classification Search ................ 427/2.14, 427/212
See application file for complete search history.

(56) References Cited

U.S. PATENT DOCUMENTS

| 4,164,109 | A | * | 8/1979 | Dubois ........................ 53/427 |
| 4,275,544 | A | * | 6/1981 | Hisazumi et al. .............. 53/433 |
| 4,302,440 | A | | 11/1981 | John et al. .................... 424/480 |
| 4,365,060 | A | | 12/1982 | Onda et al. .................... 536/65 |
| 4,611,456 | A | * | 9/1986 | Gillio-tos et al. ............. 53/427 |
| 4,928,840 | A | * | 5/1990 | Barshay et al. ................ 220/8 |
| 5,682,733 | A | * | 11/1997 | Perrone ....................... 53/560 |

\* cited by examiner

*Primary Examiner*—Elena T Lightfoot
(74) *Attorney, Agent, or Firm*—McDermott Will & Emery LLP

(57) ABSTRACT

An ingestible tablet (10), e.g. of a medicament, is enrobed to produce a tamper-evident coating by vacuum forming a film (40, 46) of material, preferably hydroxypropyl methyl cellulose, onto the surface of the tablet.

8 Claims, 3 Drawing Sheets

METHOD OF TABLET ENROBING

FIELD OF THE INVENTION

Figure 1:
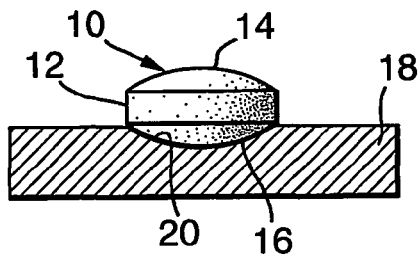

This invention concerns tablet enrobing, that is coating ingestible tablets, e.g. of a medicament, vitamin, dietary supplement etc, with suitable ingestible material so that the tablets are tamper-evident, i.e. any attempt to tamper with the tablet e.g. by adulterating the contents will result in damage to the coating that is readily visually apparent. The invention is applicable to other solid forms of medicament etc, e.g. caplets and capsules as well as tablets, but for simplicity all such forms will generally be referred to herein as tablets.

BACKGROUND TO THE INVENTION

As a safety precaution, it is nowadays becoming increasingly desirable or necessary to provide tamper-evident tablets in addition to tamper-evidence packaging for tablets of medicaments etc. It is known to enrobe tablets in gelatin for this purpose by dipping tablets into gelatin solution and allowing the solution to dry to form a coating. The gelatin solution may be coloured, and it is known to produce dual colour gelatin coatings, e.g. by coating the entire tablet with, say, yellow gelatin and then, after drying, coating half of the tablet with, say, red gelatin. This produces an attractive, tamper-evident tablet. However, the process involves several steps and is time consuming, even with single coating processes, as long drying times are involved. Further, problems are associated with use of gelatin in ingestible products as gelatin is an animal-derived material, obtained from the bones and skins of animals such as cattle, and there are increasing concerns over use of such materials in ingestible products in view of fear of animal related diseases such as Bovine Spongiform Enceptialopathy (BSE).

The present invention provides an alternative approach to tablet enrobing not necessarily using gelatin coatings.

SUMMARY OF THE INVENTION

In one aspect, the invention provides a method of enrobing a tablet, comprising vacuum forming a film of material onto the surface of the tablet.

In practising the method of the invention, the tablet and enrobing film material are exposed to conditions of differential pressure across the film, with a vacuum or substantially reduced pressure on the side of the film material in the vicinity of the tablet, so that the film material is caused to deform so as to conform to the external surface of the tablet under the action of the pressure differential, forming a skin-tight coating on at least part of the tablet surface, fitting snugly to the tablet surface. In this way a skin-tight, tamper-evident film wrapping of the tablet may be produced. In order fully to enclose the tablet in the film material, it may be necessary to perform two or more vacuum forming steps, with different parts of the tablet in the vicinity of the film material prior to exposure to the pressure differential. Vacuum chamber or vacuum bed apparatus, in which the tablet is located on a suitably shaped support and exposed to conditions of vacuum (or substantially reduced pressure) can be used for vacuum forming. Such apparatus may be based on commercially available vacuum chamber or vacuum bed apparatus. Vacuum forming techniques result in the coating forming a vacuum-tight pack around the tablet, with the exclusion of air between the coating and tablet, leading to potentially better keeping properties and hence longer shelf life of the enrobed tablet as compared with uncoated tablet.

The film should be of material that is suitable for human consumption and that has sufficient flexibility and plasticity to be vacuum formable. Some film materials have suitable properties in their natural condition, but commonly it will be necessary to pre-treat the film material so it is vacuum formable. For example, it may be appropriate to expose the film material to a solvent therefor; for instance, certain grades of polyvinyl alcohol (PVA) will vacuum form after application of a small amount of water to the surface thereof or when exposed to conditions of high humidity. A further, generally preferred, possibility is to use a film of thermoplastic material (i.e. material capable of deforming plastically on heating) with the film being heated to be in heat-softened condition prior to being thermoformed by exposure to vacuum. Suitable thermoplastic materials include modified cellulose materials, particularly hydroxypropyl methyl cellulose (HPMC) and hydroxypropyl cellulose (HPC), polyvinyl alcohol (PVA), polyethylene oxide (PEO), pectin, alginate, starches, and modified starches, and also protein films such as soya and whey protein films. The currently preferred film material is HPMC. Suitable film materials are commercially available.

When using film of thermoplastic film, the film is typically heated prior to application to the tablet (and so usually prior to exposure to the differential pressure conditions), so that the film is in heat-softened deformable condition. This can be achieved by exposing the film to a source of heat, e.g. an infra red heater, infrared lamps, a heated plate, a hot air source etc.

The film material may include optional colourings, e.g. in the form of food dyes such as F D and C yellow number 5, and/or optional flavourings, e.g. sweeteners, and/or optional textures etc in known manner.

The film material typically includes a plasticiser to give desired properties of flexibility to the film in known manner. Materials used as plasticisers include alpha hydroxy acids such as lactic acid and salts thereof, diacetin, triacetin, propylene glycol, glycerin or mixtures thereof. A typical thermoplastic film formulation is HPMC 77% by weight, plasticiser 23% by weight.

The film suitably has a thickness in the range 20 to 200 microns, conveniently 50 to 100 microns, e.g. about 80 microns, with appropriate film thickness depending on factors including the size and form of the tablet.

The method of the invention conveniently involves forming two separate, overlapping part (generally half) coatings on the tablet of the film material. Thus the method preferably involves first coating part (generally half) of the tablet, removing remaining film material not coated on the tablet, e.g. by cutting, then coating the remaining part (generally half) of the tablet, with overlapping portions of the two coatings sealed together to provide a sealed complete enclosure for the tablet, and again removing remaining surplus film material not coated on the tablet. It may be necessary to apply adhesive material or glue between the overlapping film coatings, e.g. to the surface of one or both of the film layers, to ensure formation of an effective seal therebetween and to make the enrobed tablet tamper-evident. The adhesive material conveniently has the same composition as the film, but with a greater proportion of plasticiser, e.g. 93% to 98% by weight plasticiser, so as to provide a less viscous material. The adhesive material may be applied, e.g. by use of a roller, spraying etc. A typical adhesive formulation, with % representing % by weight, is HPMC 4%, lactic acid 77%, water 19%.

The tablet conveniently includes a generally cylindrical side wall portion, with the two half coatings overlapping on this side wall. Tablets of circular symmetrical form with a circular cylindrical side wall are very common, but other forms eg generally oblong and oval, again including a cylindrical side wall, are also known.

It may also be advantageous or desirable to apply adhesive material, e.g. as described above, to the surface of the tablet prior to coating to promote adhesion of the film thereto. Again this may be achieved e.g. by use of a roller, spraying etc.

A plurality of tablets in an array may conveniently be coated simultaneously, using a suitably large sheet of film material.

In a further aspect, the invention provides a tablet enrobed by the method of the invention.

Figure 4:
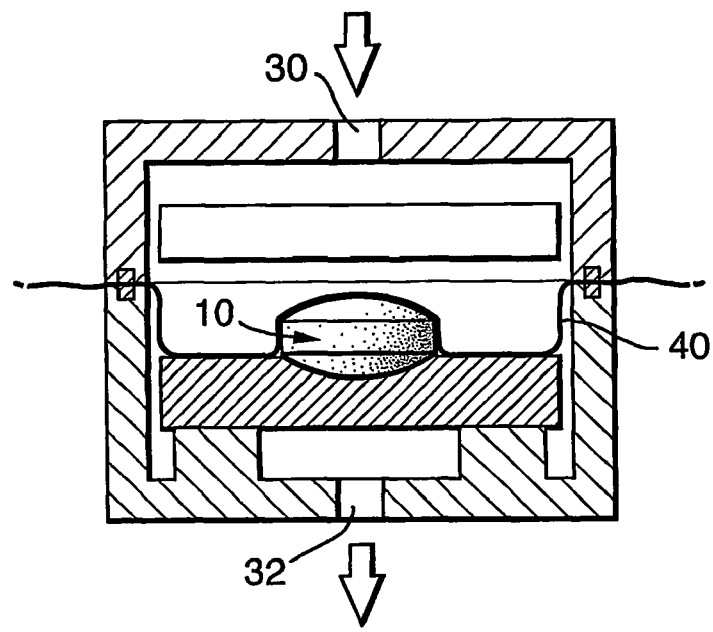
Figure 5:
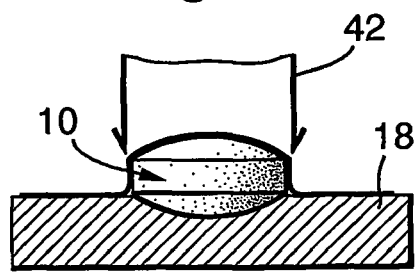
Figure 6:
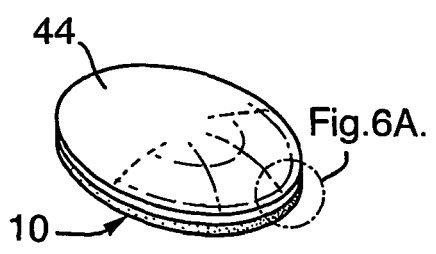
Figure 6A:
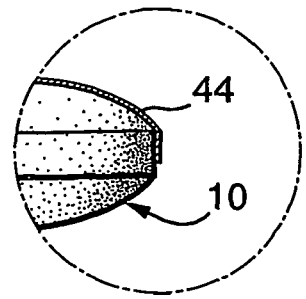
Figure 7:
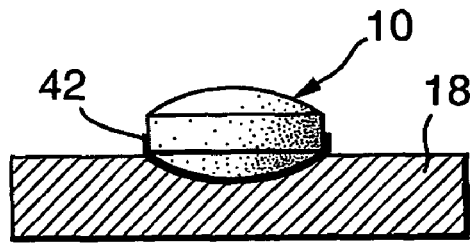
Figure 8:
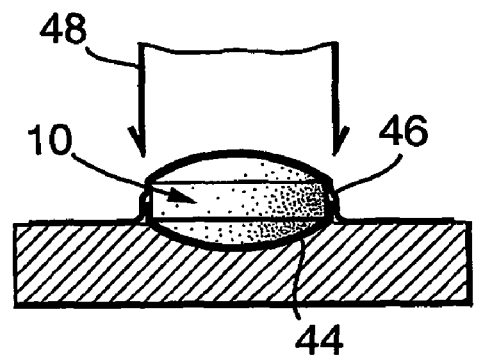
Figure 9:
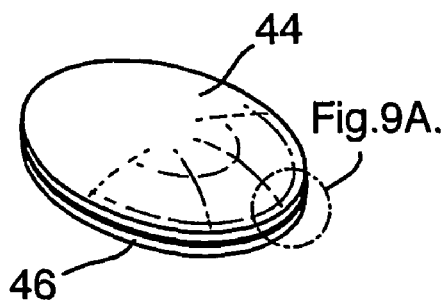
Figure 9A:
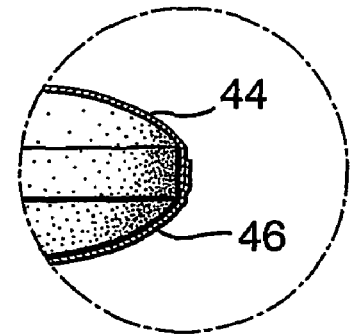

The invention will be further described by way of illustration with reference to the accompanying drawings, in which:

FIGS. 1 to 9 illustrate schematically enrobing of a tablet by a method in accordance with the invention using a split vacuum chamber, with FIGS. 1 to 5, 7 and 8 being sectional views, FIGS. 6 and 9 being perspective views on an enlarged scale and FIGS. 6A and 9A showing details of FIGS. 6 and 9, respectively, on a further enlarged scale.

DETAILED DESCRIPTION OF THE DRAWINGS

FIGS. 1 to 9 illustrate schematically a method of enrobing a tablet in accordance with the invention, using a thermoplastic film in a vacuum forming technique. In practice an array of a plurality of tablets will generally be coated simultaneously, but for simplicity only one tablet 10 is shown in these Figures.

As shown in FIG. 1, tablet 10, is of circular symmetrical form and includes a generally circular cylindrical side wall portion 12 and two similar part-spherical upper and lower portions 14 and 16.

In FIG. 1, tablet 10 is shown located on a platen or support 18 which includes a recess 20 shaped to be complementary to tablet lower portion 16 (and tablet upper portion 14).

Figure 2:
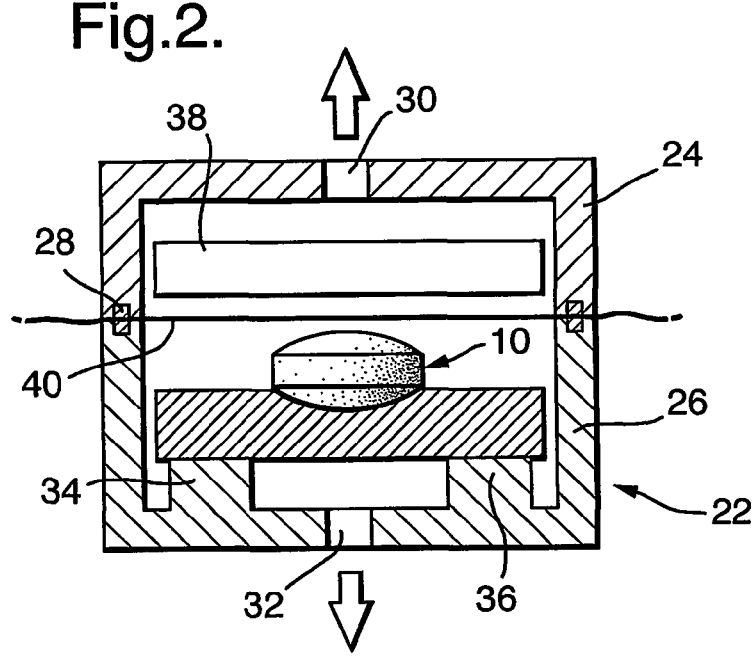

The support 18 and tablet 10 are located in a split vacuum chamber 22 of generally conventional construction, as shown in FIG. 2. The chamber is in the form of a sealed generally cuboid box, and comprises an upper chamber portion 24 and a lower chamber portion 26 that fit sealingly together, with a circumferential seal 28 therebetween. Upper chamber portion 24 includes a vacuum port 30, and lower chamber portion 26 includes a vacuum port 32, but the chamber is otherwise enclosed and sealed with respect to the exterior.

The support 18 is located on two elongate protrusions 34, 36 extending upwardly into the chamber cavity from lower chamber portion 26. A heatable plate shown schematically at 38 is located in upper chamber portion 24. A sheet 40 of hydroxypropyl methyl cellulose (HPMC) film 80 microns thick is located between the upper and lower chamber portions, trapped and secured in position between the seal 28 and chamber portions and extending outwardly therefrom. The HPMC film comprises 77% by weight HPMC, 23% by weight lactic acid plasticiser.

Figure 3:
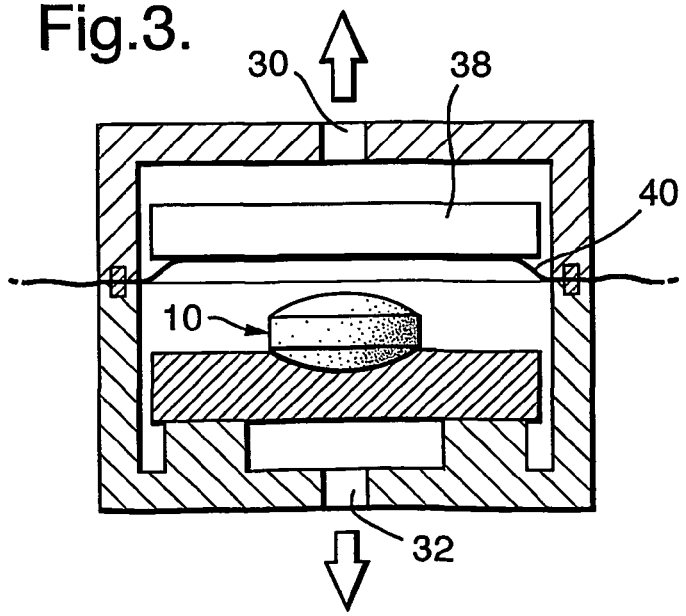

In use of the apparatus, plate 38 is heated to a temperature in the range 150 to 200° C., typically about 180° C. A vacuum is then drawn in the upper chamber, by connecting vacuum port 30 to a vacuum pump, with vacuum port 32 being left open to the atmosphere. The resulting pressure differential has the effect of drawing film 40 into contact with the lower surface of heated plate 38, as shown in FIG. 3.

A vacuum is then drawn in the lower chamber, by connecting vacuum port 32 to a vacuum pump, with the vacuum in the upper chamber being maintained. When the lower chamber is fully evacuated and the film 40 is at the correct temperature for thermoforming due to the effect of heated plate 38 (generally after about 5 seconds in contact with plate 38), air is readmitted to the upper chamber by opening vacuum port 30 to atmosphere. The resulting pressure differential has the effect of drawing film 40, which is in heat-softening condition, down onto the upper and side surfaces of the tablet 10 as shown in FIG. 4. The absence of air in the lower chamber allows the film to conform precisely to the contours of the tablet.

When the vacuum forming is complete (generally after about 10 seconds) air is readmitted to the lower chamber and the vacuum chamber is opened.

The vacuum formed web of HPMC film and tablet (retained in the web) is removed from the chamber on platen 18.

The tablet is cut out from the film web using a close-fitting hollow cylindrical blade 42, as illustrated in FIG. 5. This results in a half-enrobed tablet, as shown in FIGS. 6 and 6A, with the upper portion 14 and part of the cylindrical side wall portion 12 coated with film 44 to a point slightly below the central plane of the tablet, as shown best in FIG. 6A.

The half-enrobed tablet is put back on the platen 18 in inverted position, with the enrobed part in contact with recess 20, as shown in FIG. 7.

The platen 18 is returned to the vacuum chamber, with a further sheet 46 of the HPMC film located between the upper and lower chamber portions, in like manner to sheet 40 as described above. The vacuum forming process, as described above with reference to FIGS. 3 and 4 is repeated, and the resulting vacuum formed web of HPMC film and tablet removed from the chamber on platen 18.

The tablet is cut out of the film web using a close-fitting hollow cylindrical blade 48 of slightly larger diameter than blade 42, as illustrated in FIG. 8. This results in the tablet being fully enclosed and enrobed by the two layers of film 44 and 46, with a circumferential overlapped seal as shown in FIGS. 9 and 9A.

In order to achieve an effective seal between the overlapping film layers, glue is applied to at least one of the overlapping surfaces (e.g. to the outer surface of the cylindrical portion of film 44 coating the tablet side wall portion 12) after the first vacuum forming process and before the second vacuum forming process. The glue is of the same chemical composition as the HPMC film, but with a higher proportion of plasticiser, comprising HPMC 4% by weight, lactic acid 77% by weight and water 19% by weight. The glue is conveniently applied by use of a roller or by spraying.

In a modification of the above described apparatus and method, heated plate 38 is replaced by an array of infra red lamps in the upper chamber portion 24. In use of the apparatus a vacuum is drawn in both the upper and lower chamber portions 24 and 26 by connecting the vacuum ports 30 and 32 to a vacuum source. By maintaining equal pressures in both halves of the vacuum chamber the film sheet 40 is held in position whilst being heated by absorption of infra red radiation from the infra red lamps. This condition is maintained until the film is at the correct temperature for thermoforming. Air is then readmitted to the upper chamber portion 24 by opening vacuum port 30 to atmosphere. This modification is currently generally thought preferable to the heated plate version.

The invention claimed is:

1. A method of enrobing a tablet comprising the steps of:
providing a tablet in a first fixed position;
providing a thermoformable film;
heating the thermoformable film to a heat-softened deformable condition;
at the first fixed position, moving the thermoformable film by vacuum directly onto the contours of a portion of the tablet while maintaining the tablet in the first fixed position; at a second fixed position, moving the thermoformable film by vacuum directly onto the contours of another portion of the tablet while maintaining the tablet in the second fixed position, thereby forming a skin-tight coating on the tablet.

2. The method according to claim 1, wherein the film material is hydroxypropyl methyl cellulose.

3. The method according to claim 1, wherein the film has a thickness in the range of 20 to 200 microns.

4. The method according to claim 1 wherein the film on the tablet is formed from two separate, overlapping coating parts.

5. The method according to claim 4, comprising applying adhesive material between the overlapping coatings parts.

6. The method according to claim 5, wherein the tablet includes a generally cylindrical side wall portion, with the two coating parts overlapping on the side wall portion.

7. The method according to claim 1, comprising applying adhesive material to the surface of the tablet prior to vacuum forming of the film.

8. The method according to claim 1, wherein a plurality of tablets are coated simultaneously.

* * * * *